(12) United States Patent
Boatman

(10) Patent No.: US 7,833,259 B2
(45) Date of Patent: Nov. 16, 2010

(54) FENESTRATED ENDOLUMINAL STENT SYSTEM

(75) Inventor: Scott E. Boatman, Bloomington, IN (US)

(73) Assignee: Cook Incorporated, Bloomington, IL (US)

( * ) Notice: Subject to any disclaimer, the term of this patent is extended or adjusted under 35 U.S.C. 154(b) by 496 days.

(21) Appl. No.: 11/491,632

(22) Filed: Jul. 24, 2006

(65) Prior Publication Data

US 2007/0021822 A1 Jan. 25, 2007

Related U.S. Application Data

(60) Provisional application No. 60/702,200, filed on Jul. 25, 2005.

(51) Int. Cl.
*A61F 2/06* (2006.01)
(52) U.S. Cl. .................. 623/1.13; 623/1.15; 623/1.35
(58) Field of Classification Search ....... 623/1.11–1.16, 623/1.2, 1.23, 1.32, 1.34–1.36, 1.39, 1.17, 623/1.4
See application file for complete search history.

(56) References Cited

U.S. PATENT DOCUMENTS

| | | | |
|---|---|---|---|
| 4,562,596 A | 1/1986 | Kornberg | |
| 4,665,918 A | 5/1987 | Garza et al. | |
| 4,902,508 A | 2/1990 | Badylak et al. | |
| 4,950,227 A | 8/1990 | Savin et al. | |
| 5,104,404 A | 4/1992 | Wolff | 623/1 |
| 5,387,235 A | 2/1995 | Chuter | |
| 5,593,442 A | 1/1997 | Klein | 623/12 |
| 5,607,444 A | 3/1997 | Lam | |
| 5,711,969 A | 1/1998 | Patel et al. | |
| 5,720,776 A | 2/1998 | Chuter et al. | |
| 5,733,337 A | 3/1998 | Carr, Jr. et al. | |
| 5,855,600 A * | 1/1999 | Alt | 623/1.15 |
| 5,885,619 A | 3/1999 | Patel et al. | |
| 5,955,110 A | 9/1999 | Patel et al. | |
| 5,968,096 A | 10/1999 | Whitson et al. | |
| 6,206,931 B1 | 3/2001 | Cook et al. | |
| 6,231,598 B1 * | 5/2001 | Berry et al. | 623/1.15 |
| 6,261,319 B1 * | 7/2001 | Kveen et al. | 623/1.15 |
| 6,270,524 B1 | 8/2001 | Kim | |
| 6,348,065 B1 | 2/2002 | Brown et al. | 623/1.16 |
| 6,416,539 B1 * | 7/2002 | Hassdenteufel | 623/1.15 |

(Continued)

FOREIGN PATENT DOCUMENTS

EP 0364787 A1 4/1990

(Continued)

*Primary Examiner*—Anhtuan T Nguyen
*Assistant Examiner*—Ashley Cronin
(74) *Attorney, Agent, or Firm*—Brinks Hofer Gilson & Lione

(57) ABSTRACT

An intraluminal prosthesis is provided for strengthening a main lumen and a branch lumen in direct fluid communication with the main lumen. The prosthesis may comprise a tubular graft and a flexible stent. The tubular graft may include a flexible body having a wall with a fenestration. The flexible stent may include a body with at least one open space to encourage tissue prolapse. The flexible stent may be configured for intraluminal coupling to the fenestration of the tubular graft, so that the entire prosthesis may be assembled and anchored into a main lumen and a branch lumen with a minimally invasive procedure. The open space may encourage tissue prolapse, which may act to anchor the flexible stent to the branch lumen.

16 Claims, 18 Drawing Sheets

U.S. PATENT DOCUMENTS

| | | | |
|---|---|---|---|
| 6,464,720 B2 | 10/2002 | Boatman et al. | |
| 6,527,799 B2 | 3/2003 | Shanley | 623/1.15 |
| 6,565,600 B2 | 5/2003 | Hojeibane | 623/1.15 |
| 6,582,394 B1 | 6/2003 | Reiss et al. | 604/96.01 |
| 6,585,758 B1 | 7/2003 | Chouinard et al. | 623/1.16 |
| 6,835,203 B1 | 12/2004 | Vardi et al. | |
| 6,860,900 B2 | 3/2005 | Clerc et al. | 623/1.35 |
| 6,926,734 B1 | 8/2005 | Klein | 623/1.34 |
| 6,939,370 B2 | 9/2005 | Hartley et al. | |
| 7,163,553 B2 * | 1/2007 | Limon | 623/1.15 |
| 7,220,275 B2 | 5/2007 | Davidson et al. | 623/1.35 |
| 2001/0016766 A1 | 8/2001 | Vardi et al. | |
| 2001/0037137 A1 | 11/2001 | Vardi et al. | |
| 2003/0229389 A1* | 12/2003 | Escano | 623/1.13 |
| 2003/0233140 A1 | 12/2003 | Hartley et al. | |
| 2004/0044396 A1 | 3/2004 | Clerc et al. | 623/1.13 |
| 2004/0054396 A1 | 3/2004 | Hartley et al. | |
| 2004/0106972 A1* | 6/2004 | Deaton | 623/1.1 |
| 2004/0167607 A1 | 8/2004 | Frantzen | 623/1.13 |
| 2004/0167609 A1* | 8/2004 | Majercak | 623/1.15 |
| 2004/0254627 A1* | 12/2004 | Thompson et al. | 623/1.11 |
| 2005/0090888 A1 | 4/2005 | Hines et al. | 623/1.11 |
| 2005/0149166 A1* | 7/2005 | Schaeffer et al. | 623/1.13 |

FOREIGN PATENT DOCUMENTS

| | | |
|---|---|---|
| EP | 0421729 A2 | 4/1991 |
| EP | 0441516 A2 | 8/1991 |
| WO | WO 98/20810 | 5/1998 |
| WO | WO 98/22158 | 5/1998 |
| WO | WO 98/53761 | 12/1998 |
| WO | WO 99/29262 | 6/1999 |
| WO | WO 99/36002 | 7/1999 |
| WO | WO 03/034948 A1 | 5/2003 |
| WO | WO 03/053287 A1 | 7/2003 |
| WO | WO 2005/034807 A1 | 4/2005 |
| WO | WO 2005/099629 A1 | 10/2005 |

* cited by examiner

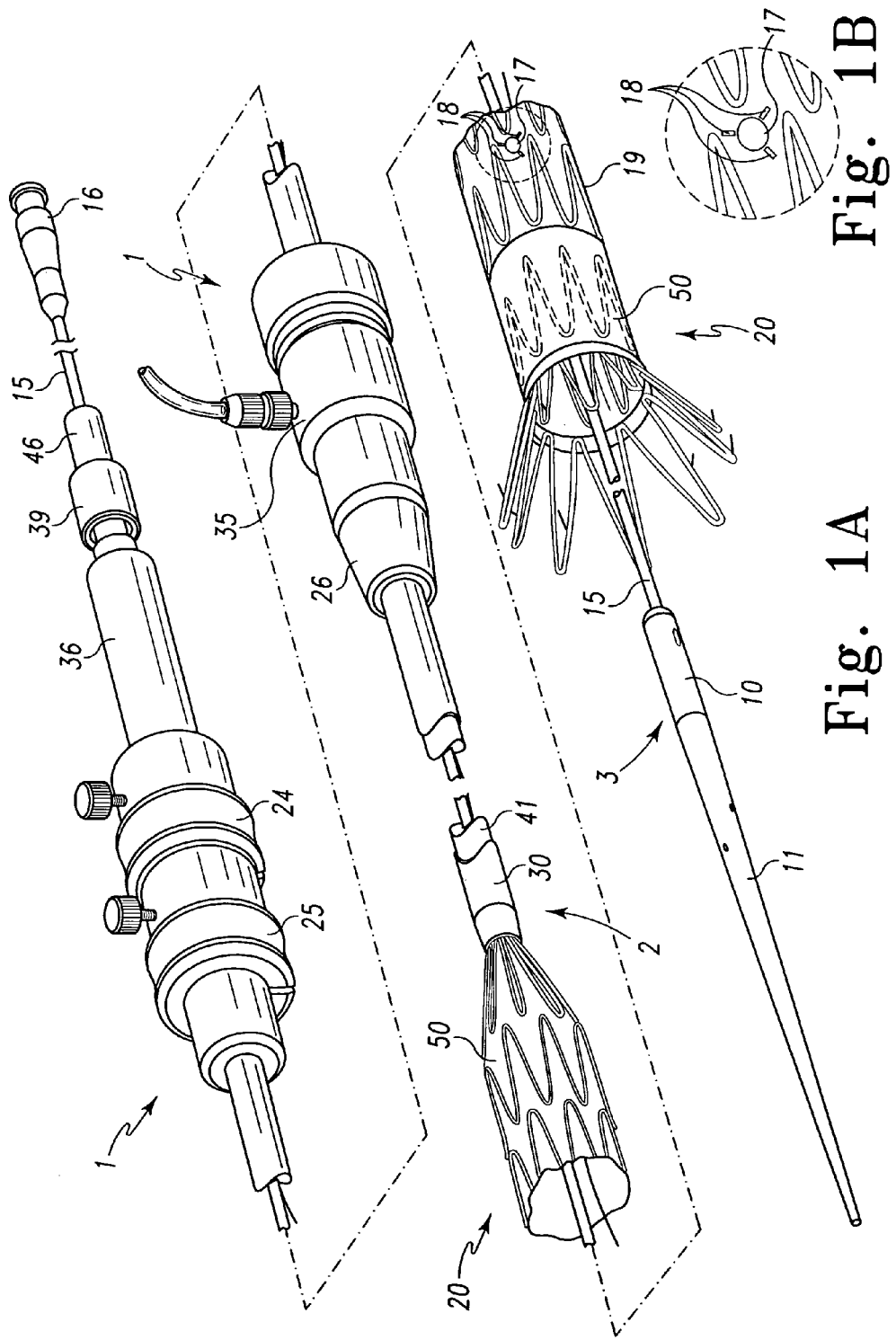

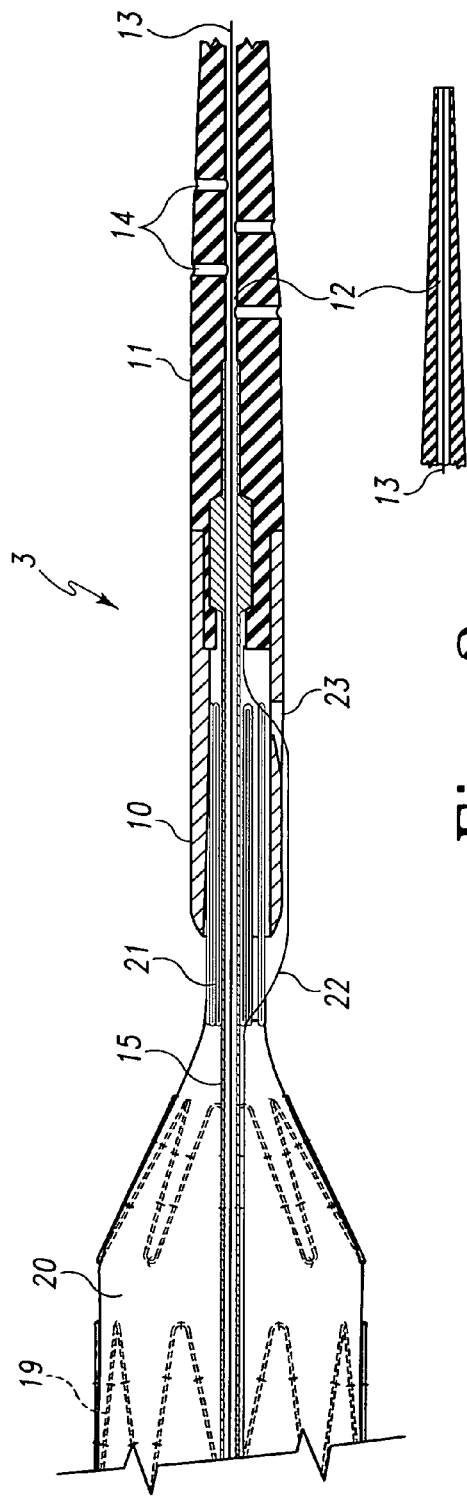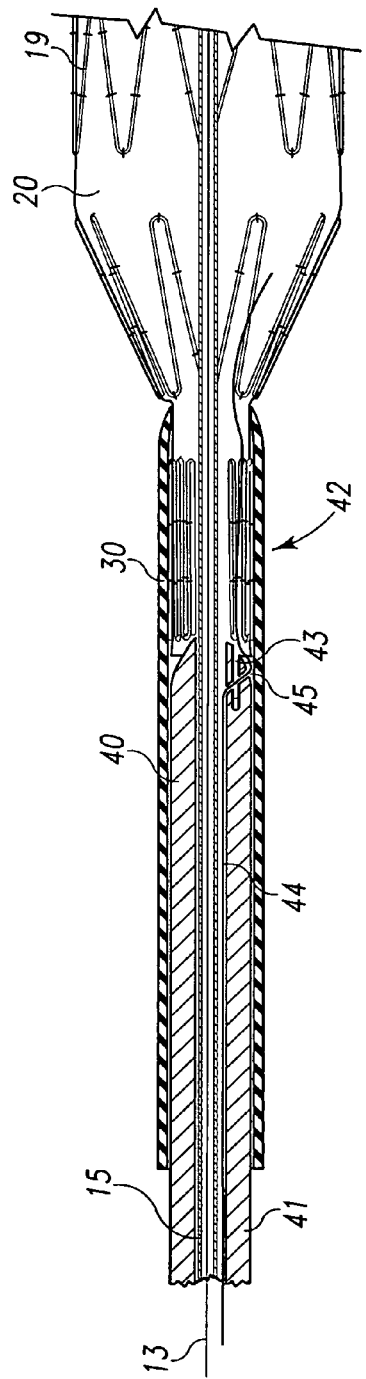

FENESTRATED ENDOLUMINAL STENT SYSTEM

CROSS-REFERENCE TO RELATED APPLICATIONS

This application is related to and claims all benefit of U.S. Provisional Application Ser. No. 60/702,200 filed Jul. 25, 2005.

BACKGROUND OF THE INVENTION

1. Technical Field

This invention relates to a medical device and, in particular, a prosthesis for implantation within the human or animal body for the repair of damaged vessels such as blood vessels.

2. Related Art

Throughout this specification, when discussing the aorta or other blood vessels, the terms distal and distally with respect to a prosthesis are intended to refer to the end of the prosthesis furthest away in the direction of blood flow from the heart. Similarly, the terms proximal and proximally are intended to mean the end of the prosthesis which when implanted would be nearest to the heart.

The functional vessels of humans, such as blood vessels and ducts, occasionally weaken or even rupture. For example, the aortic wall can weaken, resulting in an aneurysm. Upon further exposure to haemodynamic forces, such an aneurysm can rupture. A common surgical intervention for weakened, aneurismal or ruptured vessels is the use of a prosthesis to provide some or all of the functionality of the original, healthy vessel and/or preserve any remaining vascular integrity by replacing a length of the existing vessel wall that spans the site of vessel failure.

The deployment of intraluminal prostheses into the lumen of a patient from a remote location by the use of a deployment device or introducer has been disclosed in a number of earlier patents and patent applications. U.S. Pat. No. 4,562,596 entitled "Aortic Graft, Device and Method for Performing an Intraluminal Abdominal Aortic Aneurysm Repair" proposes the retention of a self expanding graft within a sleeve until it is to be deployed, at which time the sleeve is withdrawn and the graft is allowed to expand. These features and other features disclosed in U.S. Pat. No. 4,562,596 could be used with the present invention and the disclosure of U.S. Pat. No. 4,562,596 is herein incorporated by reference.

U.S. Pat. No. 4,665,918 entitled "Prosthesis System and Method" proposes a system and method for the deployment of a prosthesis in a blood vessel. The prosthesis is positioned between a delivery catheter and an outer sheath and expands outwardly upon removal of the sheath. These features and other features disclosed in U.S. Pat. No. 4,665,918 could be used with the present invention and the disclosure of U.S. Pat. No. 4,665,918 is herein incorporated by reference.

U.S. Pat. No. 4,950,227 entitled "Stent Delivery System" proposes the delivery of a stent by mounting the stent to the outside of an inflatable catheter and retaining the ends of an unexpanded stent by fitting a sleeve over either end of the stent. Expansion of the stent is caused by inflation of the catheter between the sleeves so that the ends of the stent are withdrawn from the respective sleeves and the stent released and expanded into position. These features and other features disclosed in U.S. Pat. No. 4,950,227 could be used with the present invention and the disclosure of U.S. Pat. No. 4,950,227 is herein incorporated by reference.

U.S. Pat. No. 5,387,235 entitled "Expandable Transluminal Graft Prosthesis for Repair of Aneurysm" discloses apparatus and methods of retaining grafts onto deployment devices. These features and other features disclosed in U.S. Pat. No. 5,387,235 could be used with the present invention and the disclosure of U.S. Pat. No. 5,387,235 is herein incorporated by reference.

U.S. Pat. No. 5,720,776 entitled "Barb and Expandable Transluminal Graft Prosthesis for Repair of Aneurysm" discloses improved barbs with various forms of mechanical attachment to a stent. These features and other features disclosed in U.S. Pat. No. 5,720,776 could be used with the present invention and the disclosure of U.S. Pat. No. 5,720,776 is herein incorporated by reference.

U.S. Pat. No. 6,206,931 entitled "Graft Prosthesis Materials" discloses graft prosthesis materials and a method for implanting, transplanting replacing and repairing a part of a patient and particularly the manufacture and use of a purified, collagen based matrix structure removed from a submucosa tissue source. These features and other features disclosed in U.S. Pat. No. 6,206,931 could be used with the present invention and the disclosure of U.S. Pat. No. 6,206,931 is herein incorporated by reference.

PCT Patent Publication Number No. WO99/29262 entitled "Endoluminal Aortic Stents" discloses a fenestrated prosthesis for placement where there are intersecting arteries. This feature and other features disclosed in PCT Patent Publication Number No. WO99/29262 could be used with the present invention and the disclosure of PCT Patent Publication Number No. WO99/29262 is herein incorporated by reference.

PCT Patent Publication Number No. WO03/034948 entitled "Prostheses for Curved Lumens" discloses prostheses with arrangements for bending the prosthesis for placement into curved lumens. This feature and other features disclosed in PCT Patent Publication Number No. WO03/034948 could be used with the present invention and the disclosure of PCT Patent Publication Number No. WO03/034948 is herein incorporated by reference.

United States Patent Application Publication No. 2003/0233140 entitled "Trigger Wire System" discloses release wire systems for the release of stent grafts retained on introducer devices. This feature and other features disclosed in United States Patent Application Publication No. 2003/0233140 could be used with the present invention and the disclosure of United States Patent Application Publication No. 2003/0233140 is herein incorporated by reference.

U.S. Pat. No. 6,939,370 entitled "Thoracic Aortic Stent Graft Deployment Device" discloses introducer devices adapted for deployment of stent grafts particularly in the thoracic arch. This feature and other features disclosed in U.S. Pat. No. 6,939,370 could be used with the present invention and the disclosure of U.S. Pat. No. 6,939,370 is herein incorporated by reference.

United States Patent Application Publication No. 2004-0054396 entitled "Stent-Graft Fastening" discloses arrangements for fastening stents onto grafts particularly for exposed stents. This feature and other features disclosed in United States Patent Application Publication No. 2004-0054396 could be used with the present invention and the disclosure of United States Patent Application Publication No. 2004-0054396 is herein incorporated by reference.

PCT Patent Publication Number No. WO03/053287 entitled "Stent Graft with Improved Graft Adhesion" discloses arrangements on stent grafts for enhancing the adhesion of such stent grafts into walls of vessels in which they are deployed. This feature and other features disclosed in PCT Patent Publication Number No. WO03/053287 could be used with the present invention and the disclosure of PCT Patent Publication Number No. WO03/053287 is herein incorporated by reference.

PCT Patent Publication Number No. WO98/53761 entitled "A Prosthesis and a Method and Means of Deploying a Prosthesis" discloses various embodiments of an introducer for positioning an expandable endovascular prosthesis in a lumen of a patient. This feature and other features disclosed in PCT Patent Publication Number No. WO98/53761 could be used with the present invention and the disclosure of PCT Patent Publication Number No. WO98/53761 is herein incorporated by reference.

One issue that arises with the use of an endoluminal prosthesis is where the damage in a vessel is at or near a branching vessel. For example, an abdominal aortic aneurysm may exist near the renal arteries, and a thoracic aortic aneurysm may exist near the left subclavian, common carotid, and/or innominate arteries. It would be desirable to prevent the prostheses from obstructing a branch vessel. It may also be desirable to include a fenestration in a wall of an intraluminal prosthesis to allow fluid communication between the interior cavity of the prosthesis and a branch vessel adjacent to the prostheses. It may be further desirable to maintain an alignment between such a fenestration and an opening to a branch vessel.

SUMMARY

An intraluminal prosthesis is provided for strengthening a main lumen and a branch lumen in direct fluid communication with the main lumen. The prosthesis may comprise a tubular graft and a flexible stent. The tubular graft may include a flexible body having a wall with a fenestration. The flexible stent may include a body with at least one open space to encourage tissue prolapse. The tissue prolapse may act to anchor the flexible stent to the branch lumen. The flexible stent may be configured for intraluminal coupling to the fenestration of the tubular graft, so that the entire prosthesis may be assembled and anchored into a main lumen and a branch lumen with a minimally invasive procedure. The tissue prolapse may act to anchor the flexible stent to the branch lumen.

Also provided is a flexible stent for strengthening a branch lumen. The flexible stent may include a body and a plurality of bendable tabs. The body may include first, second, and third longitudinal segments. The first and second longitudinal segments may each include a plurality of laterally interconnected cells. The third longitudinal segment may include an interconnection member and be coupled between the first and second longitudinal segments. The third longitudinal segment may include open space, so that there is open space between the first and second longitudinal segments to encourage tissue prolapse.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 1A shows a first an introducer in perspective view with a first prosthesis partially deployed.

FIG. 1B is an enlarged partial view of a portion of the first prosthesis in FIG. 1A, depicting the first prosthesis having a fenestration.

FIG. 2 shows the portion of the introducer around the proximal end of the prosthesis in detail.

FIG. 3 shows the portion of the introducer around the distal end of the prosthesis in detail.

DETAILED DESCRIPTION OF THE PREFERRED EMBODIMENTS

Figure 4:
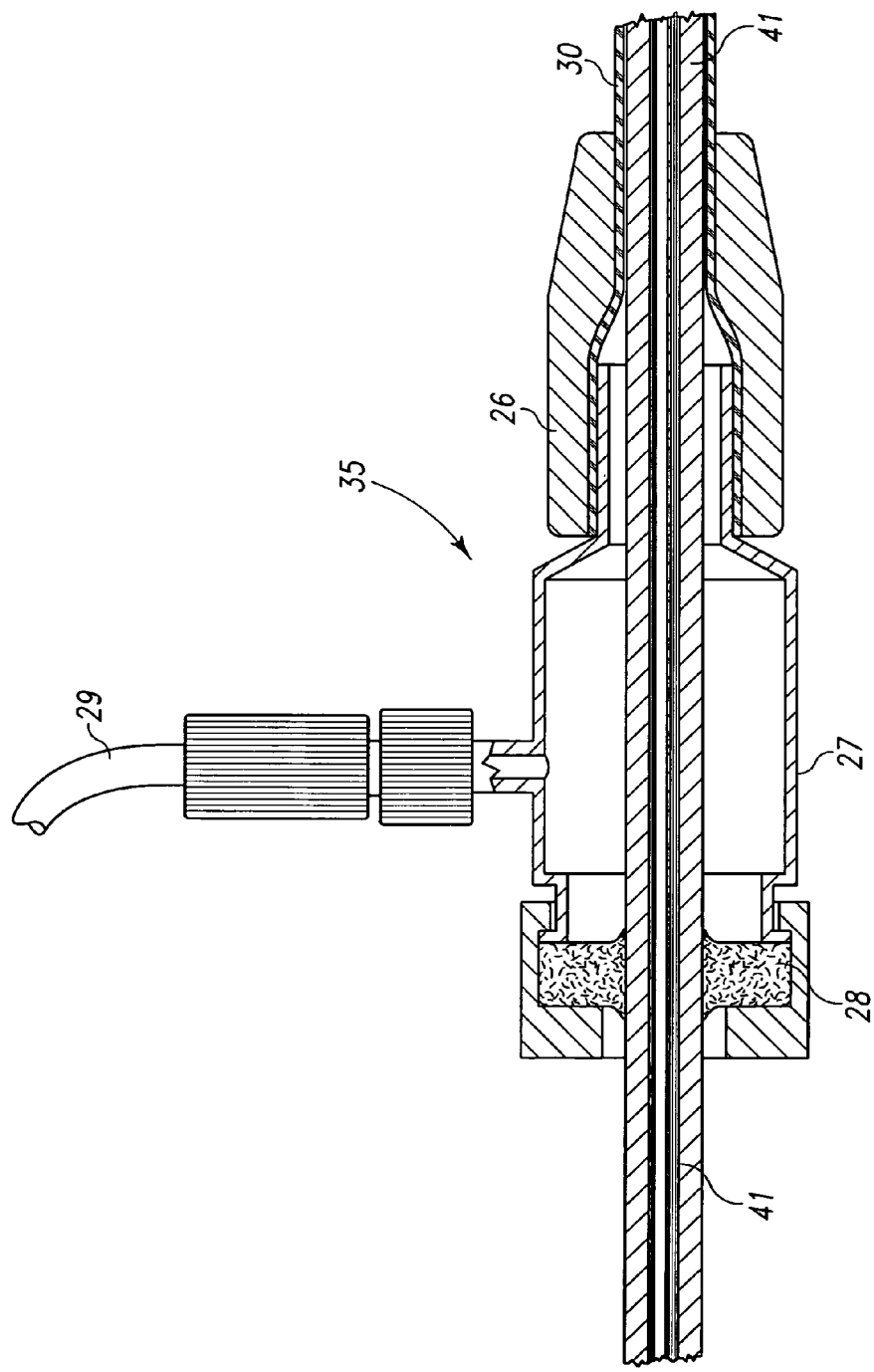
FIG. 4 shows the portion of the introducer around the haemostatic seal in detail.

FIG. 1 shows an endoluminal prosthesis 20, and an endovascular deployment system, also known as an introducer, for deploying the prosthesis 20 in a lumen of a patient during a medical procedure. The term "prosthesis" means any replacement for a body part or function of that body part. It can also mean a device that enhances or adds functionality to a physiological system. The terms "endoluminal" and "intraluminal" describe objects that are found or can be placed inside a lumen in the human or animal body. A lumen can be an existing lumens or a lumen created by surgical intervention. This includes lumens such as blood vessels, parts of the gastrointestinal tract, ducts such as bile ducts, parts of the respiratory system, etc. "Endoluminal prosthesis" thus describes a prosthesis that can be placed inside one of these lumens.

The introducer includes an external manipulation section 1, a distal positioning mechanism (attachment region) 2 and a proximal positioning mechanism (attachment region) region 3. During the medical procedure to deploy the prosthesis 20, the distal and proximal attachment regions 2 and 3 will travel through the lumen to a desired deployment site. The external manipulation section 1, which is acted upon by a user to manipulate the introducer, remains outside of the patient throughout the procedure.

The prosthesis 20 comprises a tubular graft material 50, with self expanding stents 19 attached thereto. The term "graft" means the generally cannular or tubular member which acts as an artificial vessel. A graft by itself or with the addition of other elements can be an endoluminal prosthesis. The term "stent" means any device or structure that adds rigidity, expansion force or support to a prosthesis.

The tubular graft material 50 is preferably non-porous so that it does not leak or sweat under physiologic forces. The graft material is preferably made of woven DACRON® polyester (VASCUTEK® Ltd., Renfrewshire, Scotland, UK). The tubular graft can be made of any other at least substantially biocompatible material including such fabrics as other polyester fabrics, polytetrafluoroethylene (PTFE), expanded PTFE, and other synthetic materials known to those of skill in the art. Naturally occurring biomaterials, such as collagen, are also highly desirable, particularly a derived collagen material known as extracellular matrix (ECM), such as small intestinal submucosa (SIS).

Other examples of ECMs are pericardium, stomach submucosa, liver basement membrane, urinary bladder submucosa, tissue mucosa, and dura mater. SIS is particularly useful, and can be made in the fashion described in U.S. Pat. No. 4,902,508 to Badylak et al.; U.S. Pat. No. 5,733,337 to Carr; 17 Nature Biotechnology 1083 (November 1999); and WIPO Publication WO 98/22158 of May 28, 1998, to Cook et al., which is the published application of PCT/U.S.97/14855. All of these patents and publications are incorporated herein by reference.

Respective of the origin of the graft material (synthetic versus naturally occurring), the graft material can be made thicker by making multi-laminate constructs, for example SIS constructs as described in U.S. Pat. Nos. 5,968,096; 5,955, 110; 5,885,619; and 5,711,969. All of these patents are incorporated herein by reference. In addition to xenogenic biomaterials, such as SIS, autologous tissue can be harvested as well, for use in forming the graft material. Additionally elastin or elastin-like polypeptides (ELPs) and the like offer potential as a material to fabricate the graft material.

The self expanding stents 19 cause the prosthesis 20 to expand following its disengagement from the introducer. The prosthesis 20 also includes a self expanding zigzag stent 21 that extends from its proximal end. When it is disengaged, the self expanding zigzag stent 21 anchors the proximal end of the prosthesis 20 to the lumen.

One or more fenestrations 17 may be provided in the tubular graft material 50. Radiographic markers 18 may be attached to the tubular graft material 50 adjacent to the fenestration 17 in order to aid alignment of the fenestration 17 with a branch vessel. For example, the radiographic markers 18 may be small rings of metal, such as stainless steel, sewn to the tubular graft material 50 with suture.

FIG. 2 shows the proximal attachment region 3 in greater detail. The proximal attachment region 3 includes a cylindrical sleeve 10. The cylindrical sleeve 10 has a long tapered flexible extension 11 extending from its proximal end. The flexible extension 11 has an internal longitudinal aperture 12. The longitudinal aperture 12 facilitates advancement of the tapered flexible extension 11 along an insertion wire 13. The aperture 12 also provides a channel for the introduction of medical reagents, which will flow through openings 14. For example, it may be desirable to supply a contrast agent to allow angiography to be performed during placement and deployment phases of the medical procedure.

A thin walled metal tube 15 is fastened to the extension 11. The thin walled metal tube 15 is flexible so that the introducer can be advanced along a relatively tortuous vessel, such as a femoral artery, and also to allow manipulation longitudinally and rotationally of the proximal attachment region 3. The thin walled metal tube 15 extends through the introducer to the manipulation section 1, terminating at a connection means 16, as shown in FIG. 6.

Figure 6:
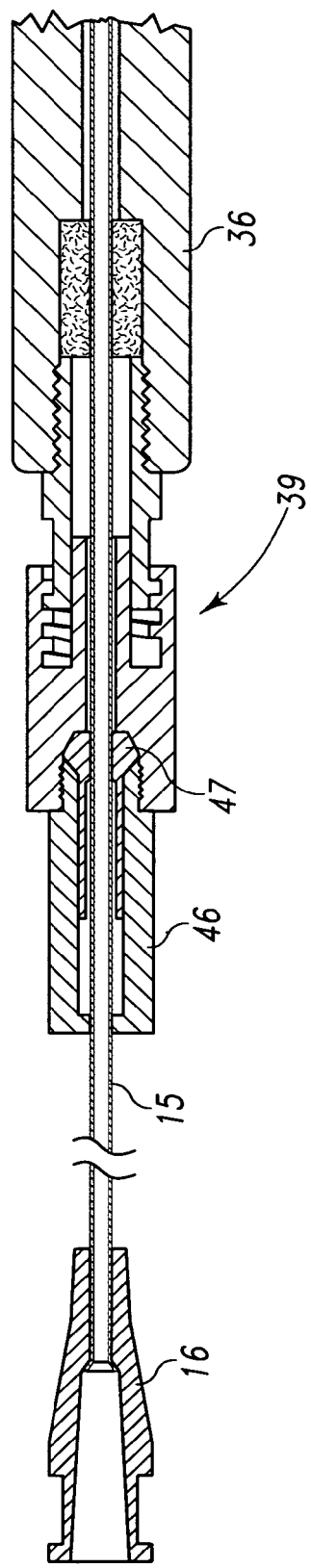
FIG. 6 shows the portion of the introducer around the pin vise clamp and the medical reagent introduction tube in detail.

Regarding the introduction of reagents, FIG. 6 also shows that the connection means 16 is adapted to accept a syringe to facilitate the introduction of reagents into the metal tube 15. The metal tube 15 is in fluid communication with the aperture 12 of the flexible extension 11. Therefore, reagents introduced into connection means 16 flow through the aperture 12 and emanate from the apertures 14.

Figure 5:
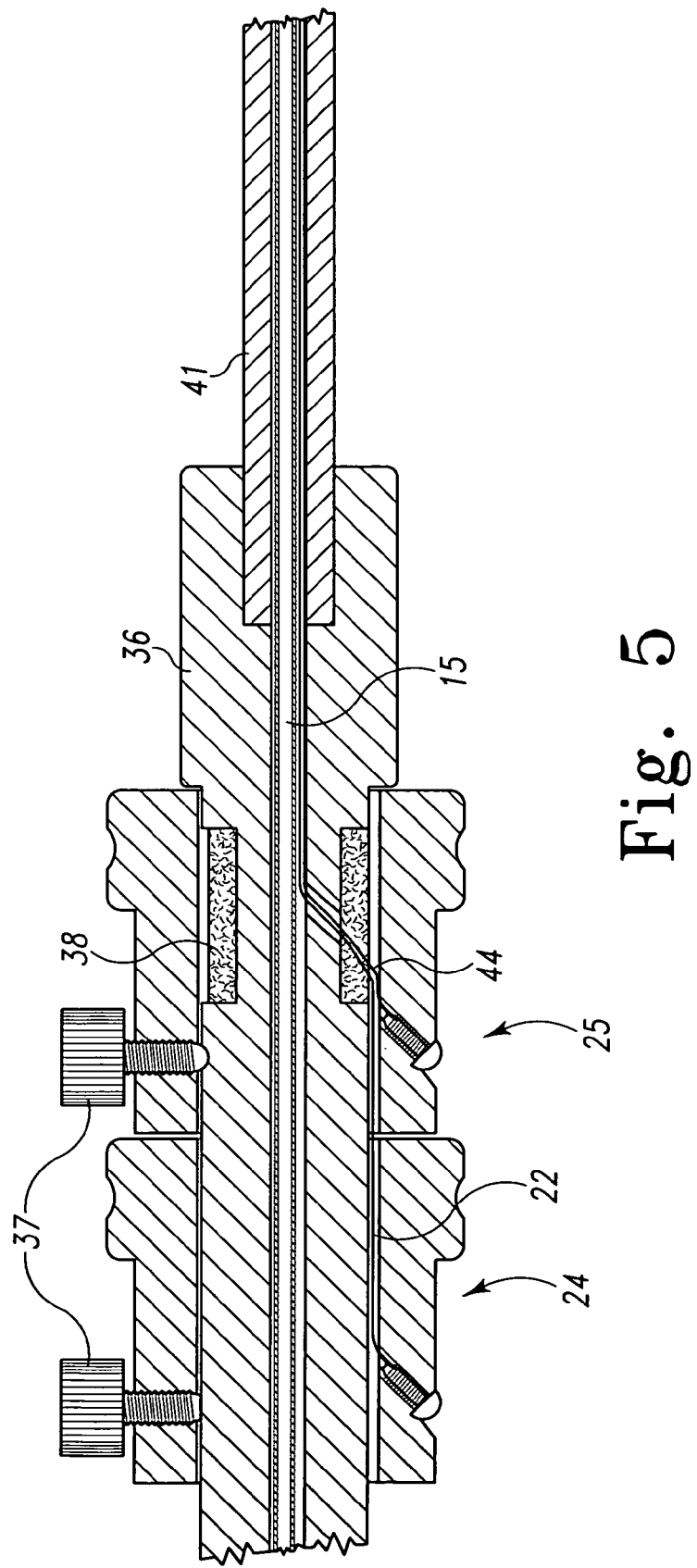
FIG. 5 shows the portion of the introducer around the trigger wire release mechanisms in detail.

As shown in FIG. 3, a plastic tube 41 is coaxial with and radially outside the thin walled metal tube 15. The plastic tube 41 is "thick walled", that is to say the thickness of its wall is several times that of the thin walled metal tube 15. A sheath 30 is coaxial with and radially outside the thick walled tube 41. The thick walled plastic tube 41 and the sheath 30 extend distally to the manipulation region 1, as shown in FIG. 5.

FIGS. 2 and 3 illustrate retention and distal and proximal release mechanisms of the introducer, respectively. During the placement phase of the medical procedure, the prosthesis 20 is retained in a compressed condition by the sheath 30. The sheath 30 extends distally to a gripping and haemostatic sealing means 35 of the external manipulation section 1, shown in FIG. 4.

During assembly of the introducer, the sheath 30 is advanced over the cylindrical sleeve 10 of the proximal attachment region 3 while the prosthesis 20 is held in a compressed state by an external force. A distal attachment (retention) section 40 is formed in the thick walled plastic tube 41 to retain the distal end of the prosthesis 20. Alternatively, the distal attachment section 40 may be a separate piece coupled to the thick walled plastic tube 41.

The self-expanding stent 21 is released by retracting the sheath 30, removing the trigger wire 22, and then sliding the proximal attachment region 3, including the retention device 10, proximally away from the stent 21. Once the retention device 10 has cleared the self-expanding stent 21, the stent 21 will expand. The trigger wire 22 and the proximal wire release mechanism 24 form a control member to selectively release the retention device 10 from the prosthesis 20 by holding the self-expanding stent 21 in the retention device 10 until the prosthesis 20 is positioned at a desired site in the lumen.

The distal end 42 of the prosthesis 20 is retained by the distal attachment section 40 of the thick walled tube 41. The distal end 42 of the prosthesis 20 has a loop 43 through which a distal trigger wire 44 extends. The distal trigger wire 44 extends through an aperture 45 in the distal attachment section 40 into the annular region between the thin walled tube 15 and the thick walled tube 41.

As shown in FIG. 5, the distal trigger wire 44 extends through the annular space between the thick walled plastic tube 41 and the thin walled tube 15 to the manipulation region 1. The distal trigger wire 44 exits the annular space at a distal wire release mechanism 25. The distal trigger wire 44 and the distal wire release mechanism 25 forms a control member to selectively disengage the distal retention section 40 from the prosthesis 20 when it is positioned at a desired site in the lumen.

FIG. 4 shows the haemostatic sealing means 35 of the external manipulation section 1 in greater detail. The haemostatic sealing means 35 includes a haemostatic seal 27 and a side tube 29. The haemostatic seal 27 includes a clamping collar 26 that clamps the sheath 30 to the haemostatic seal 27. The haemostatic seal 27 also includes a silicone seal ring 28. The silicone seal ring 28 forms a haemostatic seal around the thick walled tube 41. The side tube 29 facilitates the introduction of medical reagents between the thick walled tube 41 and the sheath 30.

FIG. 5 shows a proximal portion of the external manipulation section 1. The release wire actuation section has a body 36 that is mounted onto the thick walled plastic tube 41. The thin walled tube 15 passes through the body 36. The distal wire release mechanism 25 is mounted for slidable movement on the body 36. Similarly, the proximal wire release mechanism 22 is mounted for slidable movement on the body 36. A pair of clamping screws 37 prevents inadvertent early release of the prosthesis 20.

The positioning of the proximal and distal wire release mechanisms 24 and 25 is such that the proximal wire release mechanism 24 must be moved before the distal wire release mechanism 25 can be moved. Therefore, the distal end 42 of the prosthesis 20 cannot be released until the self-expanding zigzag stent 21 has been released and anchored to the lumen. A haemostatic seal 38 is provided so the release wires 22 and 44 can extend out through the body 36 to the release mechanisms 24 and 25 without unnecessary blood loss during the medical procedure.

FIG. 6 shows a distal portion of the external manipulation section 1. A pin vise 39 is mounted onto the distal end of the body 36. The pin vise 39 has a screw cap 46. When screwed in, the vise jaws 47 clamp against (engage) the thin walled metal tube 15. When the vise jaws 47 are engaged, the thin walled tube 15 can only move with the body 36, and hence the thin walled tube 15 can only move with the thick walled tube 41. With the screw cap 46 tightened, the entire assembly, except for the external sleeve 30, can be moved as one.

The prosthesis 20 can be deployed in any method known in the art, preferably the method described in WO98/53761 in which the device is inserted by an introducer via a surgical cut-down into a femoral artery, and then advanced into the desired position over a stiff wire guide using endoluminal interventional techniques. For example, FIGS. 7 through 12 show various stages of the deployment of the prosthesis 20 during an illustrative medical procedure. A guide wire 13 is introduced into the femoral artery and advanced until its tip is beyond the region into which the prosthesis 20 is to be deployed.

Figure 7:
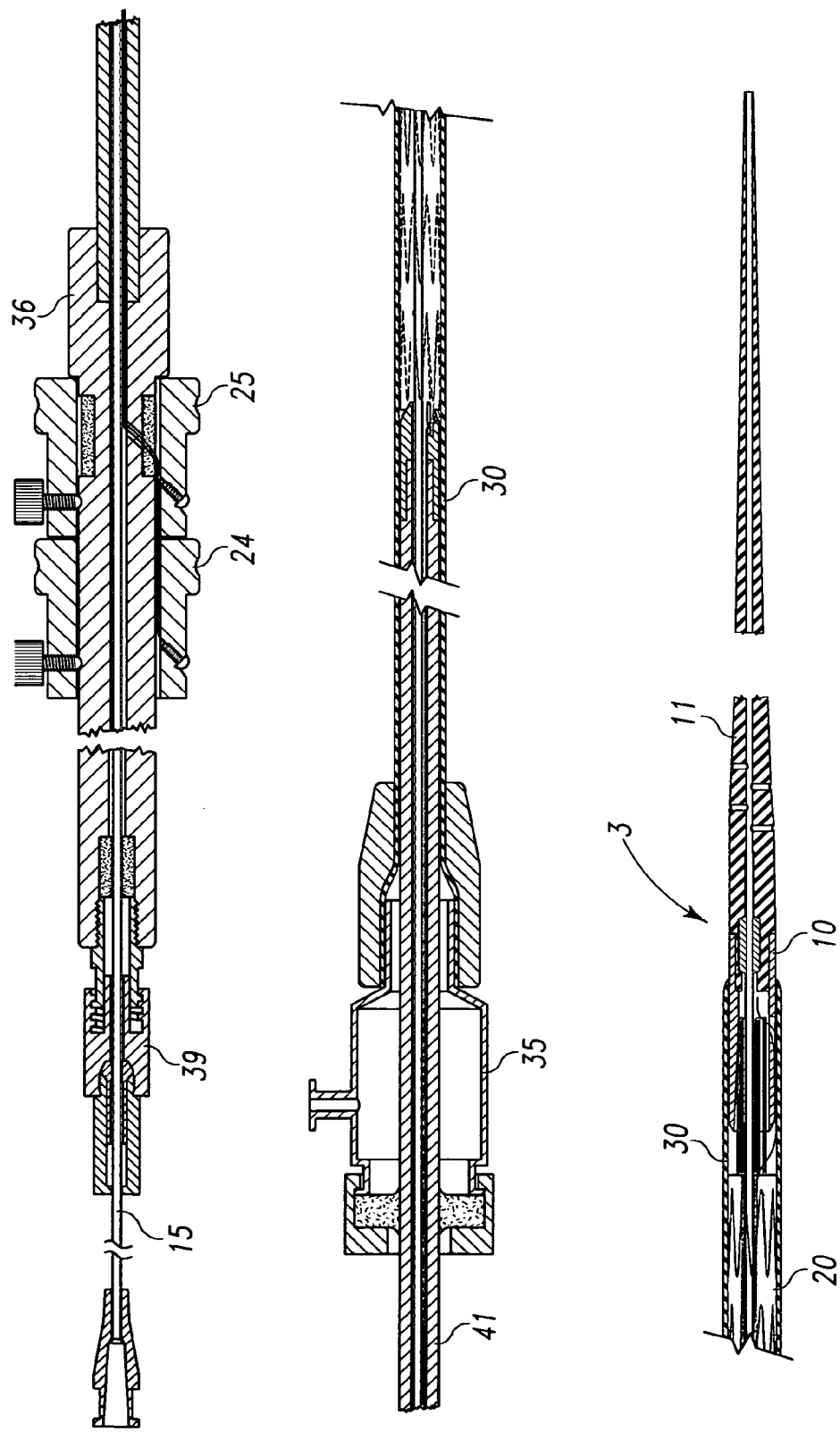
FIG. 7 shows the introducer of FIG. 1 fully loaded and ready for introduction into a patient.

In FIG. 7, the introducer assembly is shown fully assembled ready for introduction into a patient. The prosthesis 20 is retained at each of its ends by the proximal and distal retaining assemblies respectively, and compressed by the external sleeve 30. If it is an aortic aneurism which is to be grafted, the introducer assembly can be inserted through a femoral artery over the guide wire 13 in the form as shown in FIG. 7, and positioned by radiographic techniques (not discussed here). The fenestration 17 of the prosthesis 20 may be aligned with a branch vessel, such as a renal artery, during this positioning.

Figure 8:
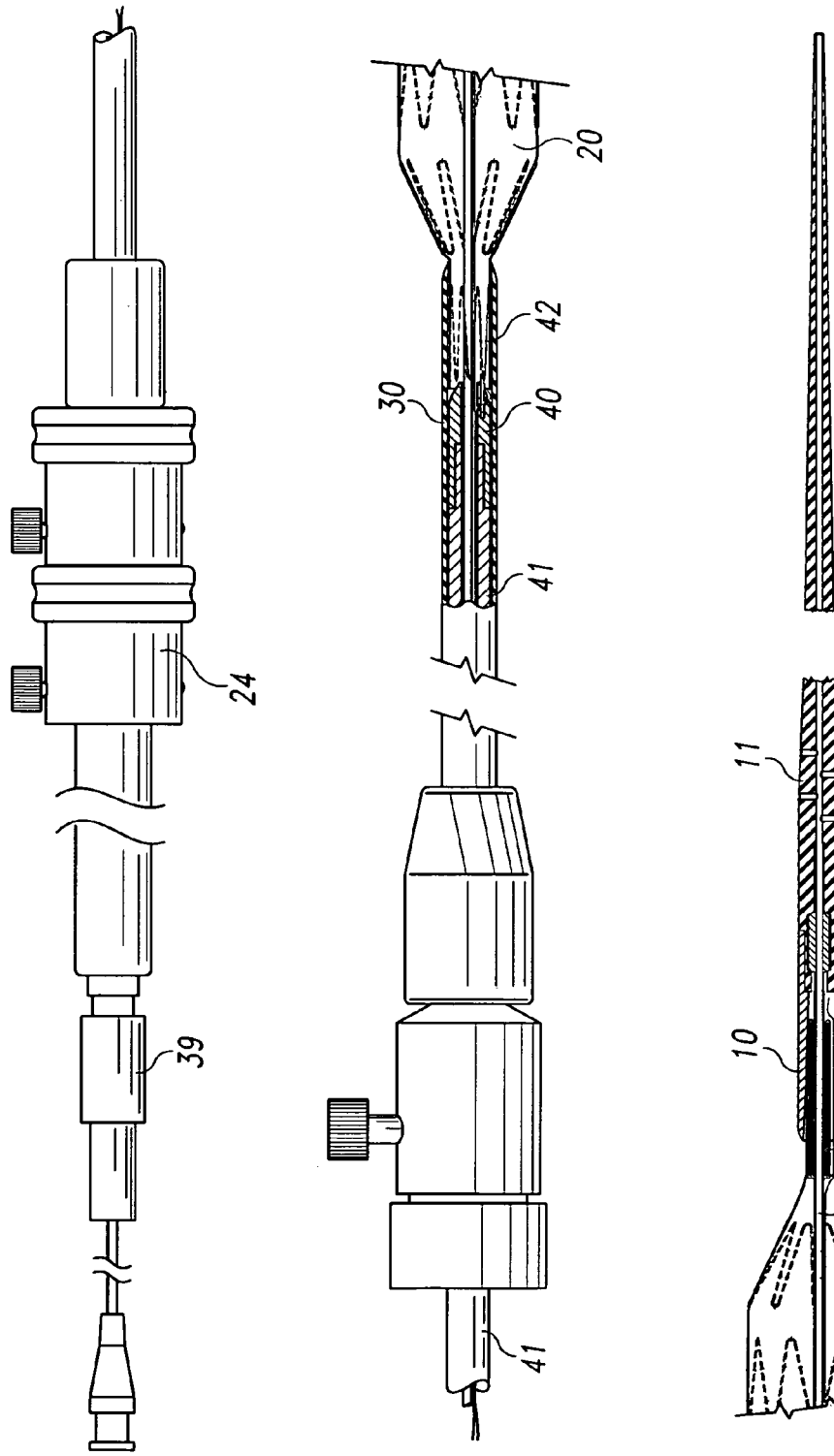
FIG. 8 shows the introducer of FIG. 7 in the next stage of deployment of the prosthesis.

In FIG. 8, the introducer assembly is in a desired position for deployment of the prosthesis 20. The external sheath 30 is withdrawn to just proximal of the distal attachment section 40. This action releases the middle portion of the prosthesis 20 so that it can expand radially. The proximal self-expanding stent 21, however, is still retained within the retention device 10. Also, the distal end 42 of the prosthesis 20 is still retained within the external sheath 30.

By release of the pin vise 39 to allow small movements of the thin walled tubing 15 with respect to the thick walled tubing 41, the prosthesis 20 may be lengthened or shortened or rotated or compressed for accurate placement in the desired location within the lumen. X-ray opaque markers (not shown) may be placed along the prosthesis 20 to assist with placement of the prosthesis.

Figure 9:
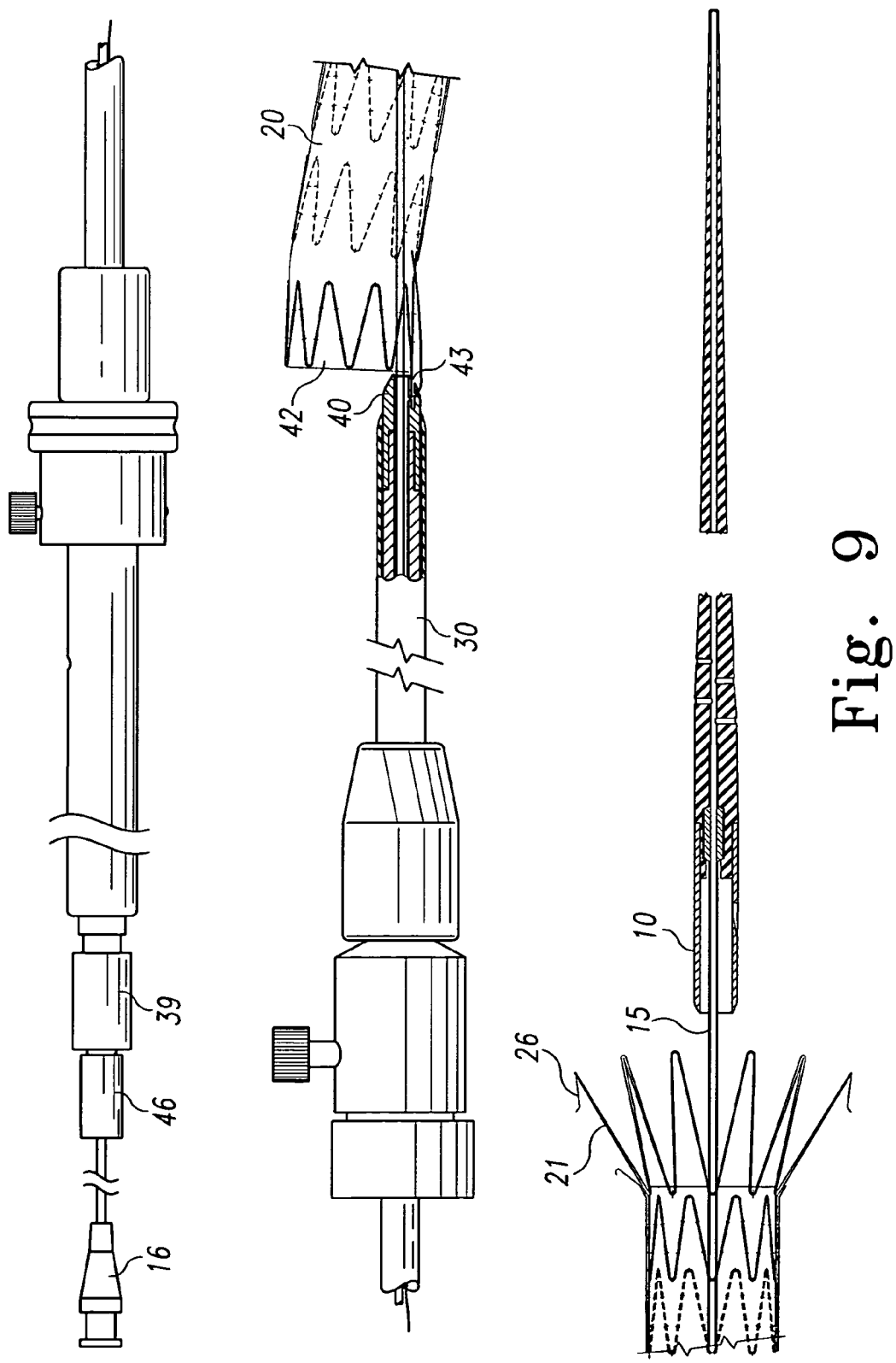
FIG. 9 shows the introducer of FIG. 7 with the release of the proximal end stage of deployment.

In FIG. 9, the proximal trigger wire 22 has been removed, allowing the retention device 10 to be separated from the self-expanding zigzag stent 21, as explained above. At this stage, the proximal trigger wire release mechanism 24 and the proximal trigger wire 22 can be removed completely.

Also, the screw cap 46 of the pin vise 39 has been loosened so that the thin walled tubing 15 can been pushed in a proximal direction to move the proximal attachment means 10 in a proximal direction. When the proximal attachment means 10 no longer surrounds the self-expanding stent 21 at the proximal end of the prosthesis 20, the self-expanding stent 21 expands. When the self-expanding stent 21 expands, the hooks or barbs 26 on the self-expanding stent 21 grip into the walls of the lumen to hold the proximal end of the prosthesis 20 in place.

At this point, the distal end 42 of the prosthesis 20 is still retained by the distal attachment means 40, with the loop 43 retained therein. The external sheath 30 is then withdrawn to distal of the distal attachment section 40 to allow the distal end 42 of the prosthesis 20 to expand.

At this point, the distal end 42 of the prosthesis 20 may still be moved. Consequently, the prosthesis 20 can still be rotated or lengthened or shortened or otherwise moved for accurate positioning. Where the prosthesis 20 to be deployed is a bifurcated graft, the movement at this stage may ensure that the shorter leg is directed in the direction of the contra-iliac artery.

Figure 10:
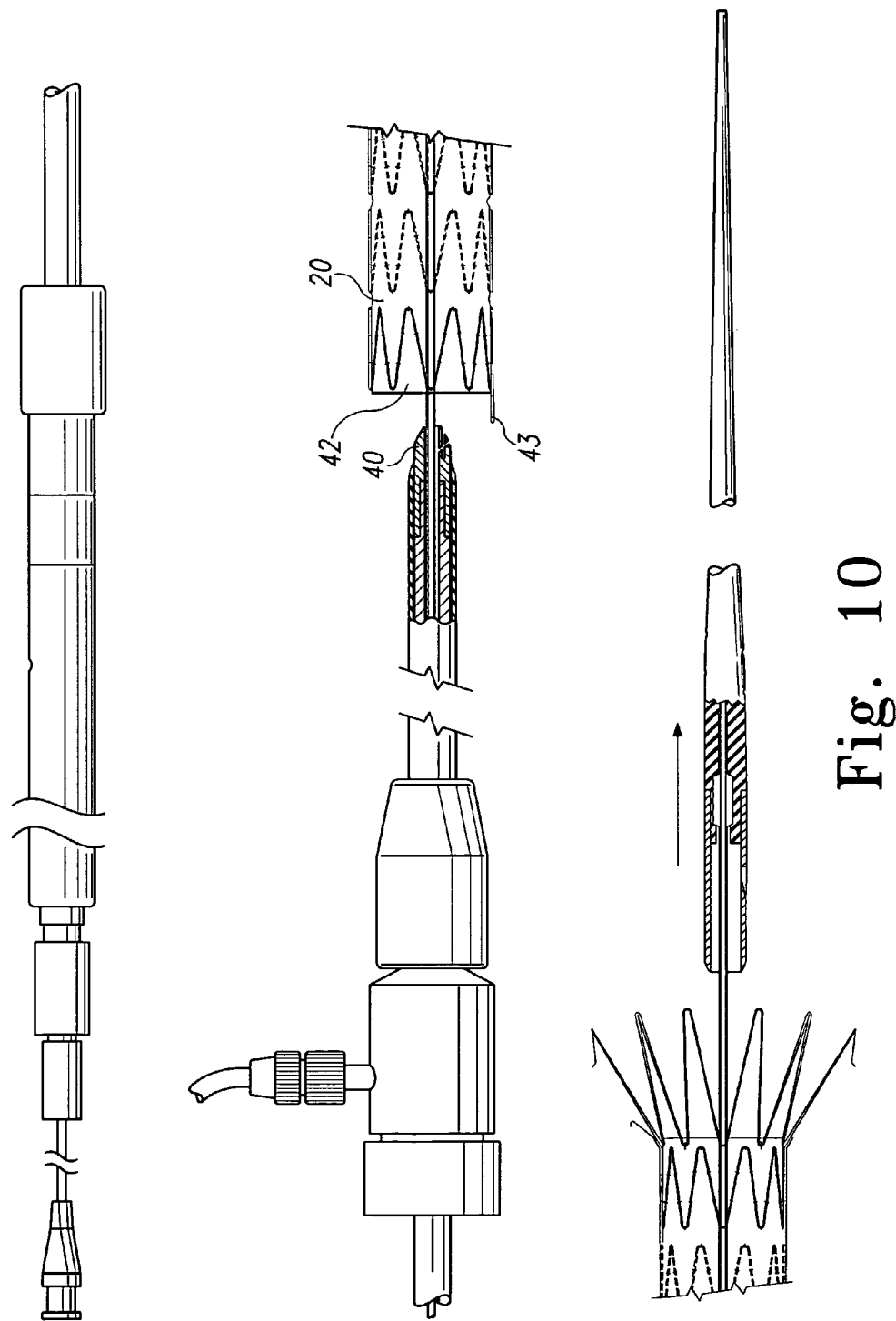
FIG. 10 shows the introducer of FIG. 7 with the release of the distal end stage of deployment.

In FIG. 10, the distal end 42 of the prosthesis 20 has been released by removal of the distal trigger wire 44. At this stage, the distal trigger wire release mechanism 25 and the distal trigger wire 44 can be removed completely. This removal may be accomplished by passing the distal wire release mechanism 25 over the pin vise 39 and the connection means 16. The loop 43 of the terminal distal self-expanding zigzag stent 19 is hence released, and the prosthesis 20 is now free to expand to the walls of the vessel. At this point, the introducer is ready to be removed.

Figure 11:
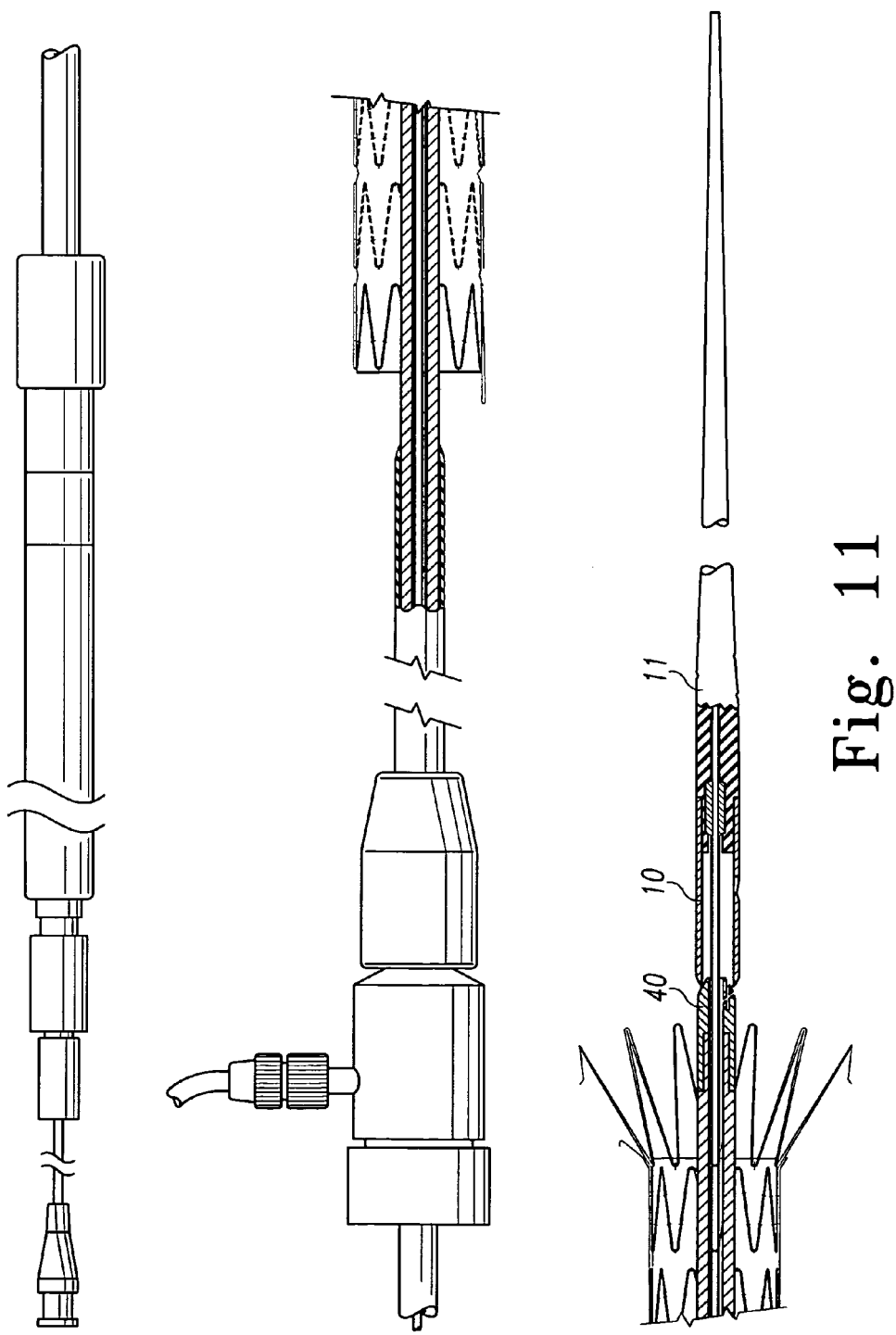
FIG. 11 shows the advancement of the distal attachment mechanism to the proximal attachment mechanism.

In FIG. 11, the first stage of removal is shown. First, the distal attachment section 40 is advanced until it is received in the rear of the proximal attachment device 10. Next, the proximal attachment device 10, the tapered flexible extension 11, and the distal attachment device 40 are removed together, as shown in FIG. 11.

Figure 12:
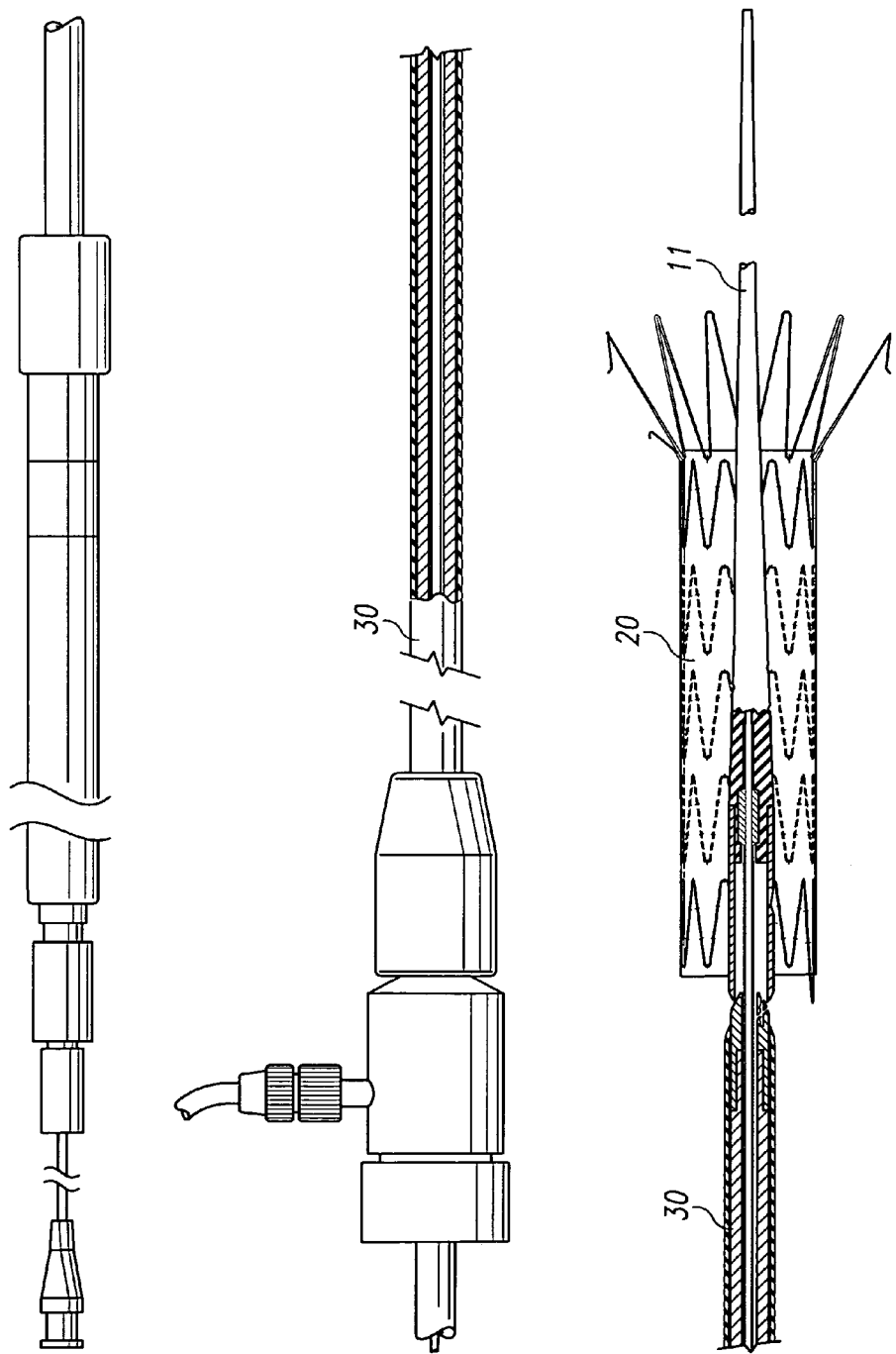
FIG. 12 shows the withdrawal of the introducer.

In FIG. 12, the sheath 30 has been advanced to uncover the joint between the proximal attachment device 10 and the distal attachment section 40. The sheath 30 may be removed with the proximal attachment device 10, the tapered flexible extension 11 and the distal attachment device 40. Alternatively, these items could be removed separately, followed by removal of the external sleeve 30.

Figure 13:
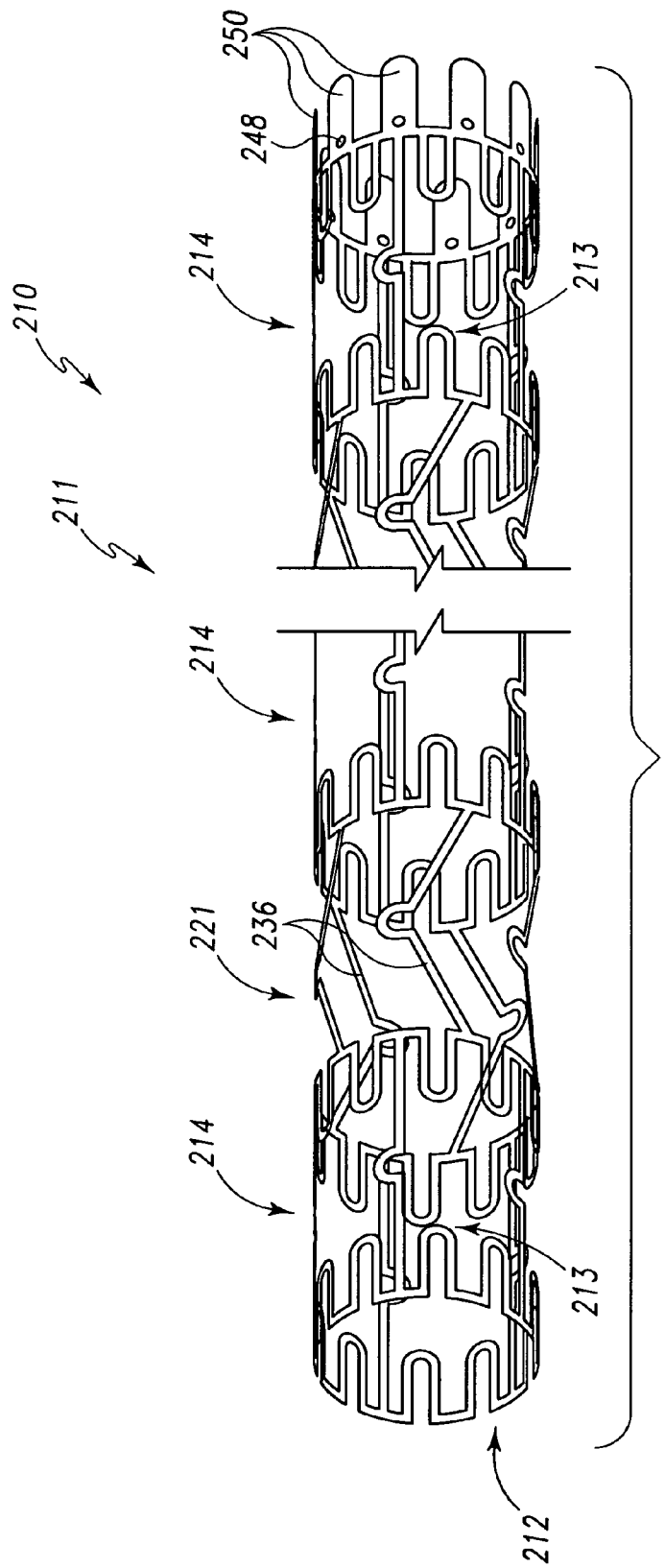
FIG. 13 is a flexible stent that is a radially expandable and laterally flexible.

FIG. 13 depicts a flexible stent 210, which is a radially expandable and laterally flexible. The flexible stent 210 is shown in FIG. 13 in an unexpanded state. The flexible stent 210 is configured to have an outer diameter approximately equal to the diameter of fenestration 17 of the prosthesis 20, so that the flexible stent 210 may be tightly coupled to the prosthesis 20, as shown in FIG. 20.

The flexible stent 210, which is comprised of an elongated member 211 with a passage 212 extending longitudinally therethrough, is formed from a tube of malleable, biocompatible material such as stainless steel. By annealing the stainless steel, the metal is soft and plastically deformable to allow the stent 210 to be readily radially expanded using a balloon catheter. The endoluminal flexible stent 210 may be similar in construction to stents disclosed in U.S. Pat. No. 6,464,720 entitled "Radially Expandable Stent", which is herein incorporated by reference.

The major difference between the flexible stent 210 and stents disclosed in U.S. Pat. No. 6,464,720 and elsewhere is that the flexible stent 210 is designed to encourage tissue prolapses between stent elements, whereas usually stents are designed to prevent tissue prolapses. The reason that the flexible stent 210 is designed thusly is so that tissue prolapses may help anchor the flexible stent 210 to the lumen.

Figure 15:
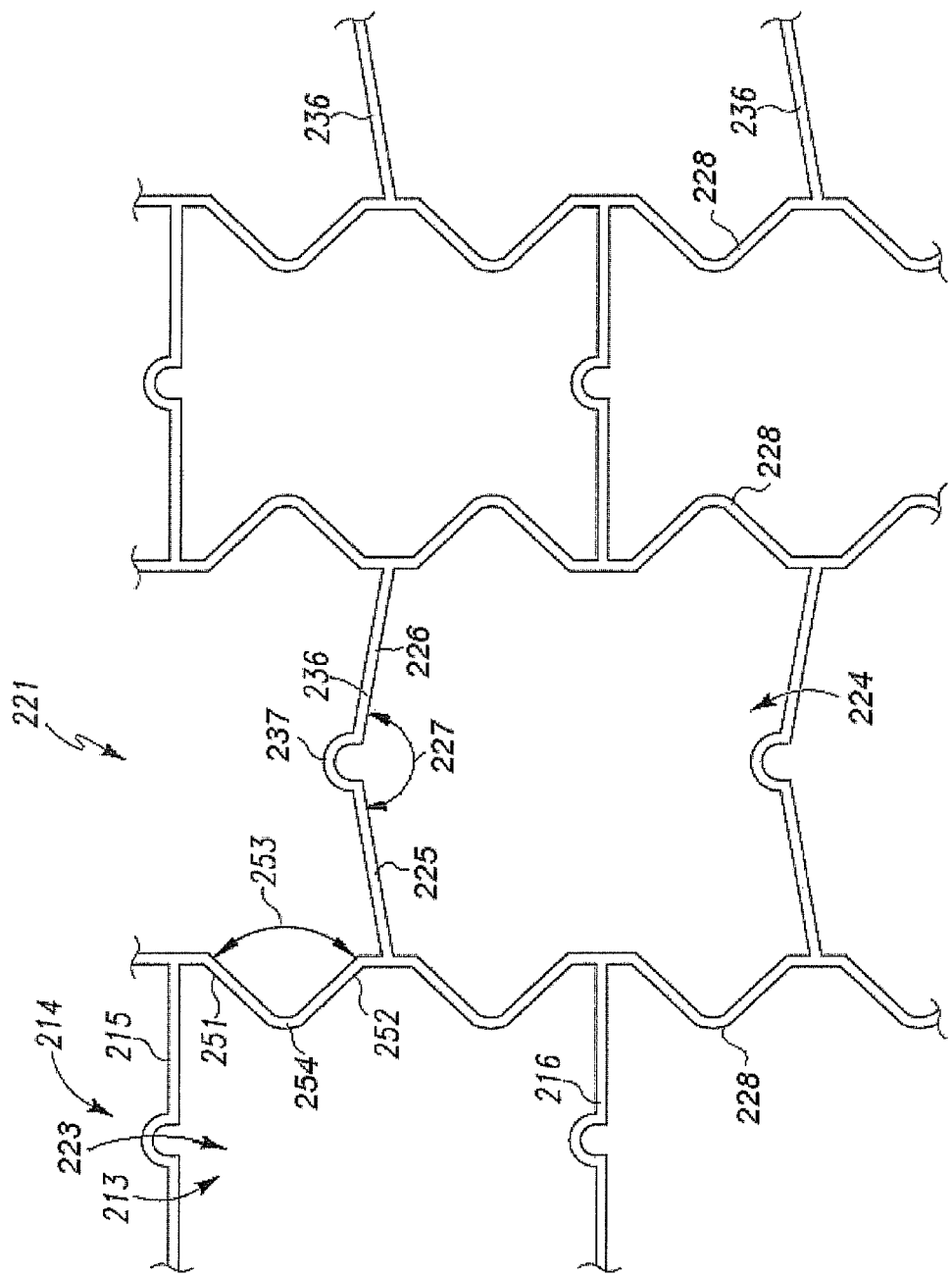
FIG. 15 is an enlarged side view of closed cells of the flexible stent of FIG. 13 in an expanded state.

The flexible stent 210 includes a repeating series of first and second alternating segment types. The first segment type is a longitudinal segment 214 having a plurality of laterally interconnected closed cells 213, which each cell 213 defining a first open space 223. The second segment type is a flexible interconnection segment 221 that interconnects adjacent longitudinal segments via at least one interconnection strut, member, or tab 236. The longitudinal segments 214, when expanded, provide the flexible stent 210 with the radial strength required to maintain patency of a lumen or vessel such as a vein, an artery, or a duct. The interconnection segments 221 provide the flexible stent 210 with lateral flexibility necessary for placement through or into tortuous vessels or sites that are subject to many bending cycles over a large range of angles. The interconnection member 236 is circumferentially spaced from adjacent interconnection members in order to define a second open space 224 between the interconnection members 236 and the longitudinal segments 214. The interconnection member 236 includes a first arm 225 and a second arm 226. The first arm 225 can be coupled between the longitudinal segment 214 and tab 237 and the second arm 226 can be coupled between tab 237 and another longitudinal segment 214. In an unexpanded state, the first and second arms 225, 226 are angled relative to one another at an angle 227, which increases to a greater angle, up to 180 degrees, when in the expanded state, as shown in FIG. 15.

To form the alternating longitudinal segments 214 and 221 from a metal tube or sheet, material must be removed in some manner, such as by a commercially available computer-controlled laser, leaving a framework of integrated support members that has a small surface area relative to the initial surface area of the tube or sheet. Other methods of manufacture include chemical etching using photoresistive masking techniques, machining, electrode discharge machining (EDM), or cutting with a water jet.

The flexible stent 210 also includes tabs 250 at an end thereof. The tabs 250 may be bent radially outward from flexible stent 210 to secure the flexible stent 210 to the prosthesis 20, as shown in FIGS. 20 and 21. The flexible stent 210 preferably includes at least one radio opaque marker 248, which is preferably positioned near the tabs 250.

Figure 14:
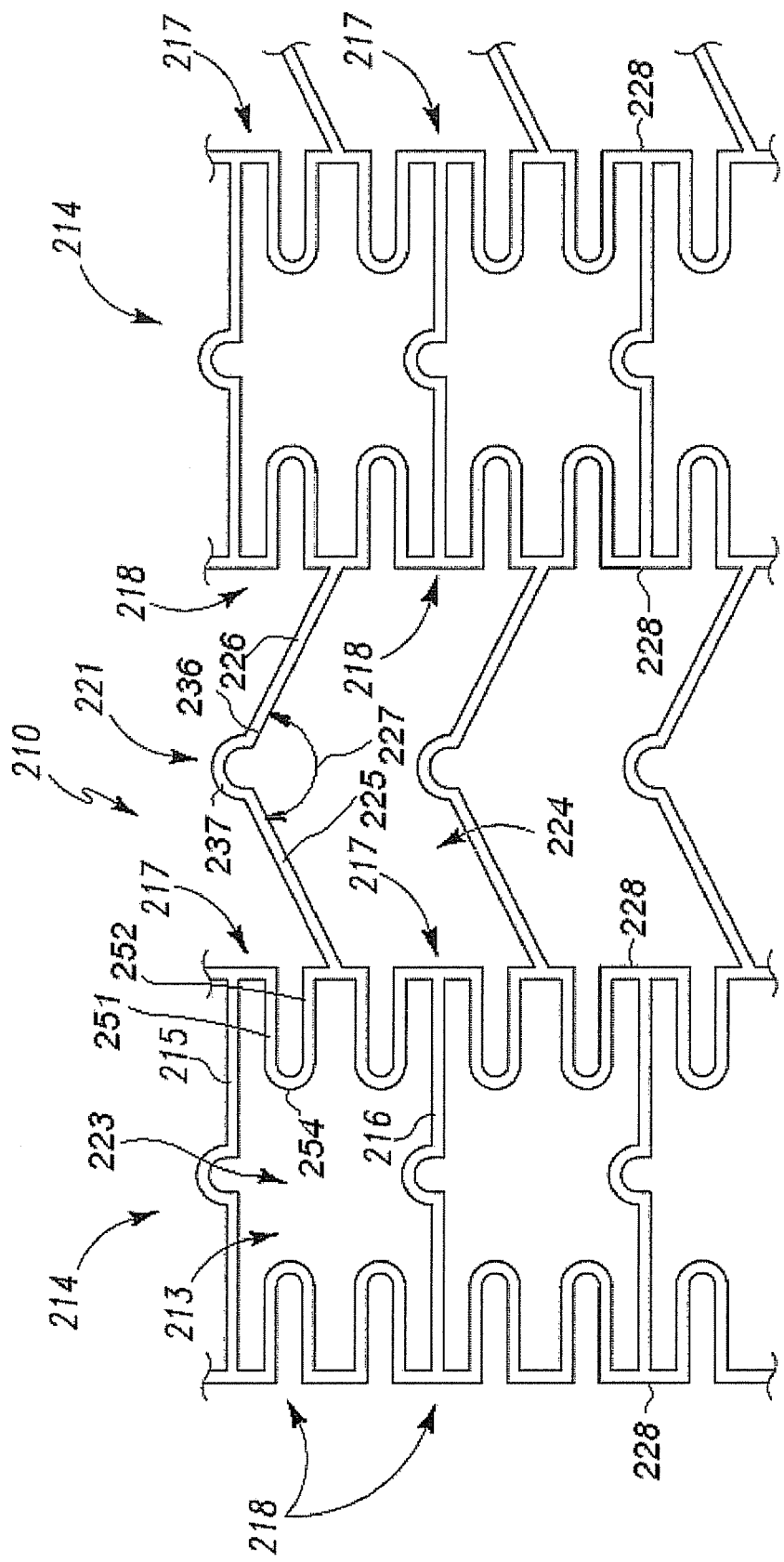
FIG. 14 is an enlarged side view of closed cells of the flexible stent of FIG. 13 in an unexpanded state.

FIG. 14 depicts closed cells 213 of the flexible stent 210 of FIG. 13 in an unexpanded state. Each closed cell 213 includes a pair of longitudinal struts 215 and 216 that are circumferentially spaced from one another, which maintain longitudinal orientation during and after expansion of the flexible stent 210. The longitudinal struts 215 and 216 are typically shared with the two laterally adjacent cells, which are interconnected with additional closed cells 213 to form a longitudinal segment 214. Alternatively, open cells or a combination of open and closed cells can be used. The first and second longitudinal struts 215 and 216 are interconnected at both ends 217 and 218 at longitudinal edges 228 that include a plurality of arms 251, 252 interconnected by a plurality of bends 254 in a serpentine pattern.

Figure 15A:
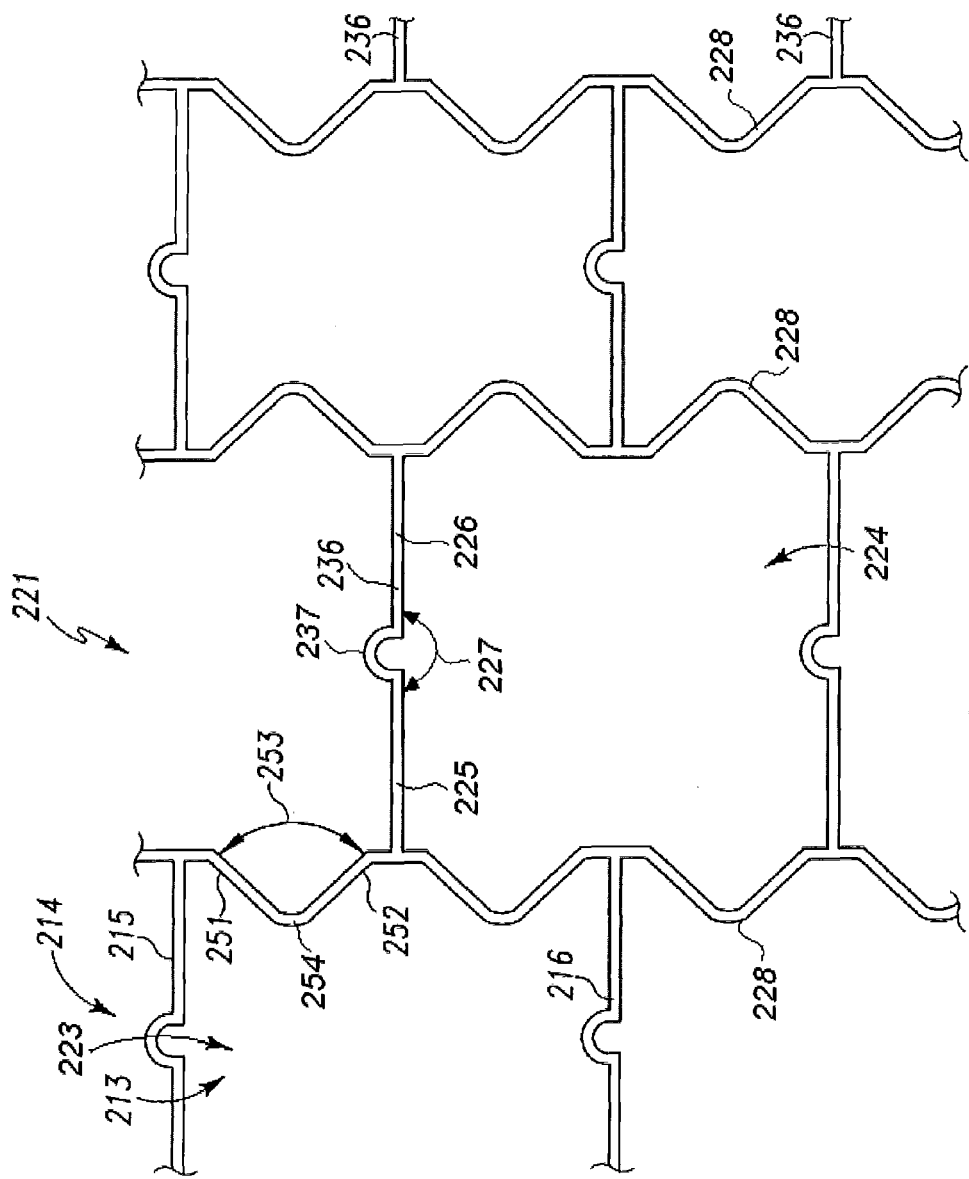
FIG. 15a is an enlarged side view of closed cells of the flexible stent of FIG. 13 in an expanded state, with arms of an interconnection member at about 180 degrees.
Figure 15B:
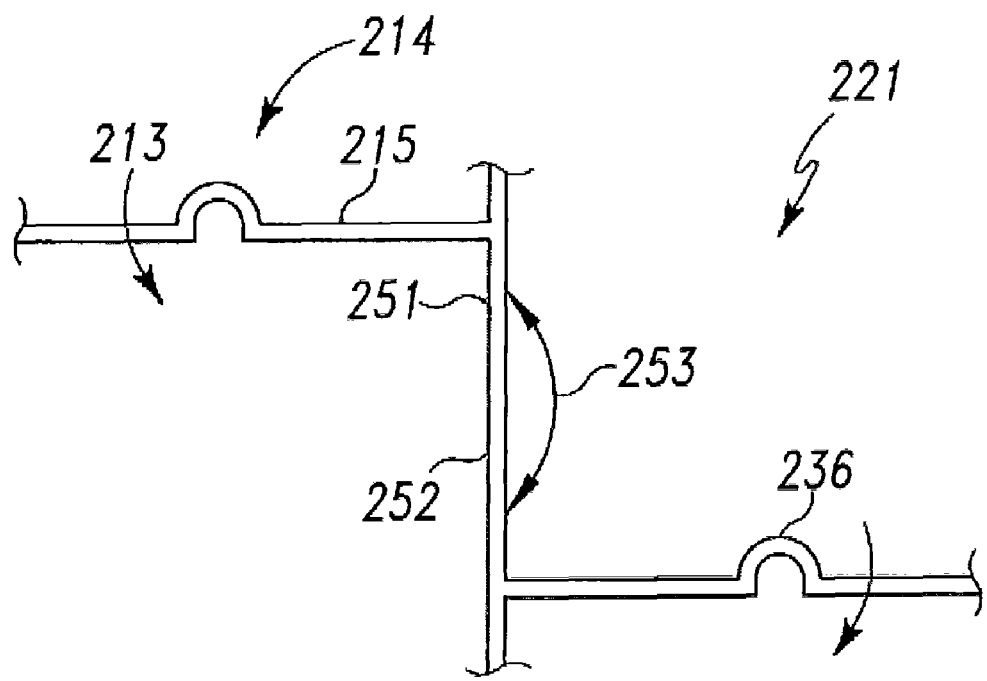
FIG. 15b is an enlarged partial side view of closed cells of the flexible stent of FIG. 15a in an expanded state, with folded arms at about 180 degrees.

FIG. 15 depicts an enlarged, side view of closed cells 213 of the flexible stent 210 of FIG. 13 in an expanded state. The cells 213 of the longitudinal segments 214 are defined between the longitudinal struts 215, 216 and the longitudinal edges 228. In the unexpanded state, the arms 215, 216 can be parallel to one another. At full expansion of the flexible stent 210, the angle 253 between folded arms 251 and 252 approaches 180 degrees and the angle 227 between the arms 225, 226 of the interconnection member 221 approaches 180 degrees such that the second open space 224 has a substantially rectangular shape. FIG. 15a illustrates the angle 227 between arms 225 and 226 at about 180 degrees. FIG. 15b is an enlarged partial view of FIG. 15a, with the angle 253 between arms 251 and 252 at about 180 degrees. Although radial strength is increased as the angle between the arms 251 and 252 increases, additional stresses placed at the points of their attachment to the longitudinal struts 215, 216 or 236 make the preferable final angle closer to 90 degrees.

The closed cells 213 allow the nominally-sized flexible stent 210 to be deployed at different diameters within a given range. The expanded diameters preferred for use in peripheral and non-coronary applications such the aorta, iliac, femoral, popliteal, renal, subclavian, and carotid arteries or vein graft and other venous lesions, generally range from 4.0 to 14.0 mm. The preferred length of the flexible stent 210 would be 7 to 60 mm length, although even longer lengths could be used.

Figure 16:
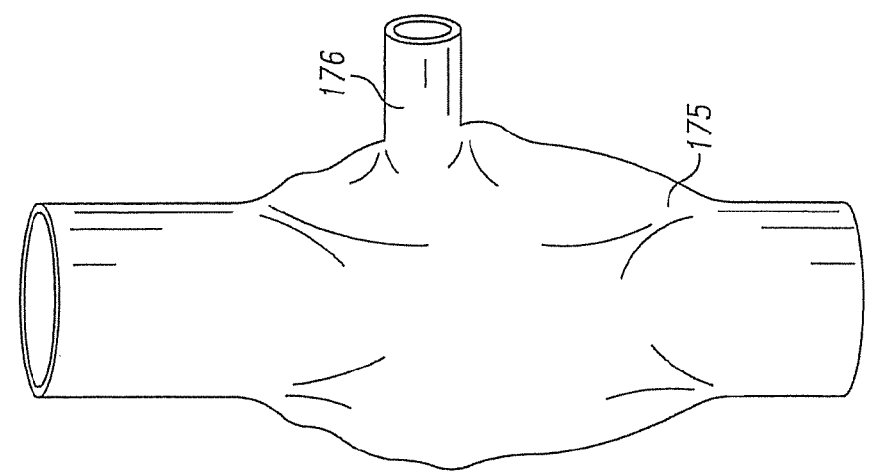
FIG. 16 is a front view of a main lumen and a branch lumen fluid communication with the main lumen.
Figure 17:
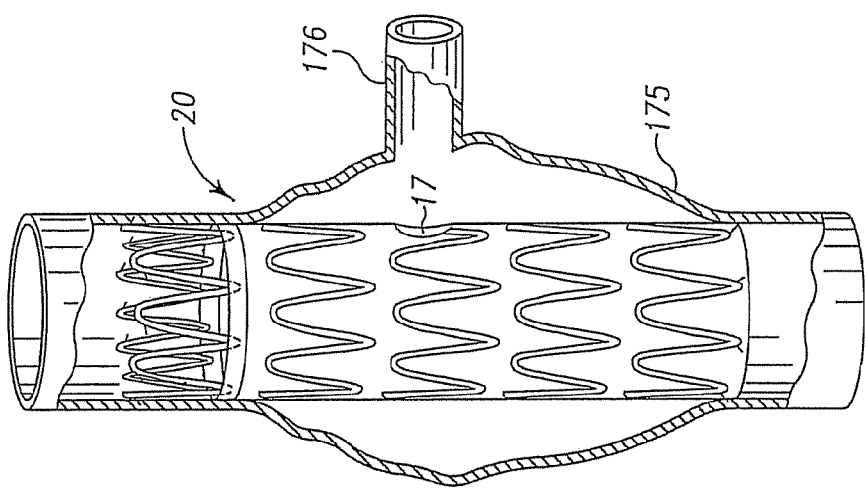
FIG. 17 is a front view of the main lumen and the branch lumen of FIG. 17 after the prosthesis of FIG. 1 has been implanted.
Figure 18:
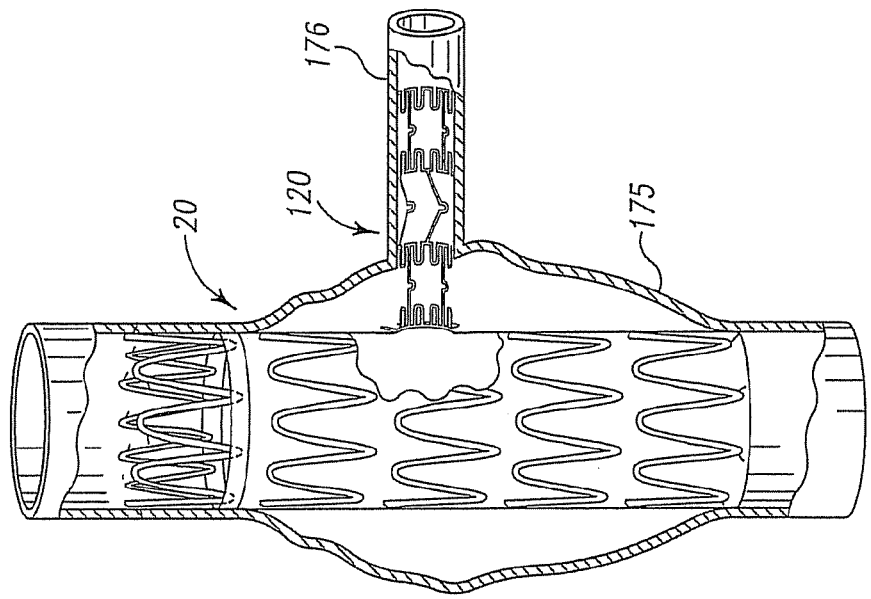
FIG. 18 is a front view of the main lumen and the branch lumen of FIG. 17 after both the prosthesis of FIG. 1 and the prosthesis of FIG. 13 have been implanted.

FIG. 16 is a front view of a main lumen 175 and a branch lumen 176, wherein the lumens 175 and 176 are in fluid communication. The main lumen 175 has an aneurism, or weakness, and exists at the attachment point of the branch lumen 176. FIG. 17 shows the lumens 175 and 176 after the prosthesis 20 has been successfully implanted. The fenestration 17 is aligned with the opening of the branch lumen 176. The prosthesis 20 reinforces the main lumen 175. FIG. 18 shows the lumens 175 and 176 after the flexible stent 210 has been successfully implanted. The flexible stent 210 performs two main functions. First, the flexible stent 210 keeps the fenestration 17 aligned so that the lumens 175 and 176 remain in fluid communication. Second, the flexible stent 210 reinforces the branch lumen 176, which may also be weakened because of the aneurism.

Figure 19:
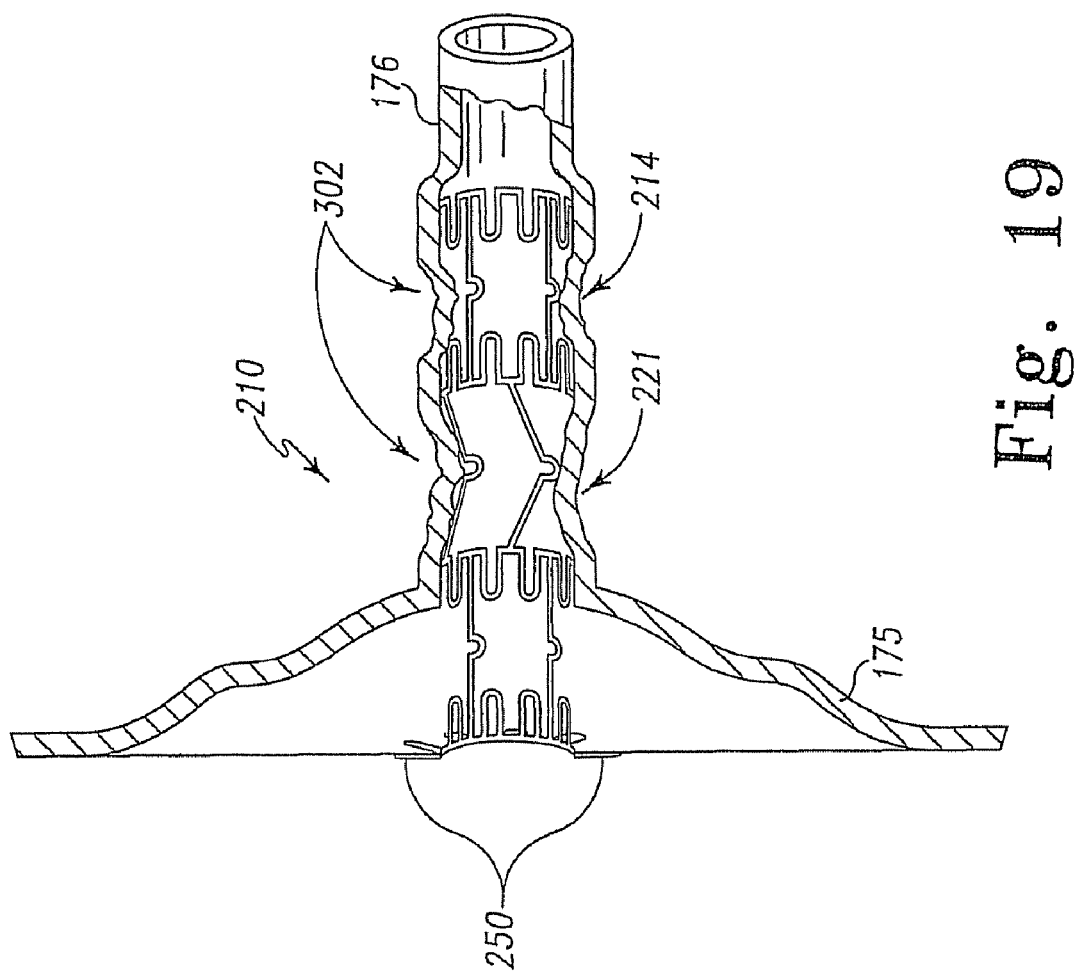
FIG. 19 is a detailed front view of the prosthesis of FIG. 13 after implantation.

FIG. 19 shows the implanted flexible stent 210 in more detail. Because the second open spaces 224 of the longitudinal segments 221 contain a significant amount of open space, typically more than the first open spaces 223, tissue prolapses 302 develop in the lumen 176 to fill the void. These tissue prolapses 302 exert force on the longitudinal segments 214, so that the entire flexible stent 210 is anchored to the lumen 176 thereby.

The flexible stent 210 can be implanted at the desired location by crimping the flexible stent 210 onto a conventional angioplasty balloon and locating the balloon at the desired location. The flexible stent 210 can then be expanded by the balloon at the desired location in a manner similar to a conventional angioplasty stent. The tabs 250 are shown in FIGS. 18 and 19 bent radially outward from the body 211 of the stent 210. Such bending of the tabs 250 may be accomplished by locating the balloon in the lumen 176, and then "over inflating" the balloon. Alternatively, another balloon device may be used that is particularly suited for bending the tabs 250.

Throughout this specification, unless the context requires otherwise, the words "comprise" and "include" and variations such as "comprising" and "including" will be understood to imply the inclusion of an item or group of items, but not the exclusion of any other item or group items.

While various embodiments of the invention have been described, it will be apparent to those of ordinary skill in the art that many more embodiments and implementations are possible within the scope of the invention. Furthermore, although various indications have been given as to the scope of this invention, the invention is not limited to any one of these but may reside in two or more of these combined together. Accordingly, the invention is not to be restricted except in light of the attached claims and their equivalents.

The invention claimed is:

1. An intraluminal prosthesis for strengthening a main lumen and a branch lumen in direct fluid communication with the main lumen, the prosthesis comprising:
a tubular graft comprising a flexible body having a wall with a fenestration; and
a flexible stent comprising a body having a radially expandable elongated member with a passage extending longitudinally therethrough, the flexible stent being expandable from an unexpanded state to an expanded state, the body having at least one interconnection member coupled between a first longitudinal segment and a second longitudinal segment, each of the longitudinal segments including a plurality of laterally interconnected cells, each cell of said longitudinal segment defining a first open space with a first area, and wherein the at least one interconnection member defines lateral edges of a second open space and the first and second longitudinal segments define longitudinal edges of the second open space, the second open space having a second area larger than the first area through the side of the flexible stent, wherein the second area of the second open space, when the flexible stent is in the expanded state, is sized to receive a sufficient amount of tissue prolapse therethrough and within the passage to anchor the flexible stent within said branch lumen,
wherein the flexible stent is intraluminally coupled to the fenestration of the tubular graft, wherein the at least one interconnection member includes a first arm coupled to the first longitudinal segment and a second arm coupled to the first arm and the second longitudinal segment, where, when the flexible stent is in the unexpanded state, the first and second arms are angled relative to each other at a first angle, wherein, when the flexible stent is in the expanded state, the first and second arms are angled relative to each other at a second angle greater than the first angle, wherein the first angle increases to the second angle of 180 degrees during expansion of the flexible stent.

2. The intraluminal prosthesis of claim 1 wherein the tubular graft further comprises a plurality of self expanding stents that are coupled along the length of the flexible body of the tubular graft.

3. The intraluminal prosthesis of claim 1 wherein the flexible stent body comprises alternating longitudinal segments.

4. The intraluminal prosthesis of claim 1 wherein the flexible stent comprises a plurality of bendable tabs coupled to a longitudinal end of the flexible stent body.

5. The intraluminal prosthesis of claim 4 wherein each of the bendable tabs is configured to bend substantially radially outwardly from the flexible stent body when a force is applied to the bendable tab from an inside of the flexible stent body.

6. The intraluminal prosthesis of claim 5 wherein the flexible stent comprises a radio opaque marker coupled to the body of the flexible stent near one of the bendable tabs.

7. The intraluminal prosthesis of claim 6 wherein the tubular graft further comprises a self expanding stent mounted to and extending beyond an end of the flexible body of the tubular graft.

8. The intraluminal prosthesis of claim 7 further comprising a plurality of self expanding stents that are coupled along the length of the flexible body of the tubular graft,
wherein the self expanding stent mounted to the end of the flexible body includes attachment barbs.

9. The intraluminal prosthesis of claim 1, wherein at least one of the longitudinal segments comprises at least one longitudinal strut separating the laterally interconnected cells, the at least one longitudinal strut having a first arm and a second arm coupled to the first arm, where, when the flexible stent is in the unexpanded state or the expanded state, the first and second arms of the at least one longitudinal strut maintain their longitudinal orientation.

10. The intraluminal prosthesis of claim 9, wherein at least one of the longitudinal segments further comprises a plurality of arms and bends interconnecting the arms in a serpentine pattern to form the longitudinal edges of the second open space, the longitudinal edges coupled to the at least one longitudinal strut and one of the arms of the at least one interconnection member.

11. The intraluminal prosthesis of claim 10, wherein, when the flexible stent is in the unexpanded state, the arms of the longitudinal edges are substantially parallel to one another, and, when the flexible stent is in the expanded state, the arms of the longitudinal edges are angled relative to each other at an angle of about 90 degrees to about 180 degrees.

12. The intraluminal prosthesis of claim 11, wherein the angle between said arms of the longitudinal edges, when the flexible stent is in the expanded state, is substantially 180 degrees.

13. The intraluminal prosthesis of claim 12, wherein the second open space is substantially rectangular when the flexible stent is in the expanded state.

14. The intraluminal prosthesis of claim 9, wherein the at least one interconnection member comprises a plurality of interconnection members oriented to define a plurality of laterally connected cells that have the second open space with the second area, wherein said cells of the longitudinal segments and said cells of the interconnection members are longitudinally separated by the longitudinal edges.

15. The intraluminal prosthesis of claim 1, wherein the first area of the first open space, when the flexible stent is in the expanded state, is sized to receive a sufficient amount of tissue prolapse therethrough and within the passage such that the flexible stent is anchored within said branch lumen.

16. The intraluminal prosthesis of claim 1, wherein the flexible stent is a balloon-expandable stent.

* * * * *